United States Patent
Flannery et al.

[11] 3,973,966
[45] Aug. 10, 1976

[54] PHOTOCHROMIC COMPOSITION CONTAINING A DIPHENYL DIBENZOCHROM-3-ENE

[75] Inventors: John B. Flannery, Webster; Anita C. Van Laeken, Rochester, both of N.Y.

[73] Assignee: Xerox Corporation, Stamford, Conn.

[22] Filed: May 8, 1974

[21] Appl. No.: 468,110

[52] U.S. Cl................ 96/48 R; 96/48 QP; 96/119 PQ; 96/1.5; 96/90 PC; 252/300; 260/239 R; 260/345.2; 260/327 R; 260/327 H
[51] Int. Cl.[2]............................. G03C 1/52
[58] Field of Search .......... 96/90 PC, 1.5; 252/300; 260/239 R, 345.2, 327 R, 327 H, 48 R, 48 QP, 119 QP

[56] References Cited
UNITED STATES PATENTS
3,359,103  12/1967  Becker et al...................... 96/90 PC
3,642,479  2/1972  Van Allan et al. ............... 96/90 PC

*Primary Examiner*—Won H. Louie, Jr.
*Attorney, Agent, or Firm*—James J. Ralabate; James P. O'Sullivan; Jerome L. Jeffers

[57] ABSTRACT

Disclosed are novel imaging imaging comprising photochromic compounds of the formula:

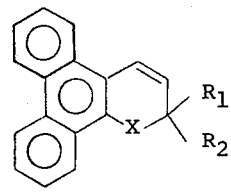

wherein X is selected from the group consisting of oxygen, sulfur and selenium; and wherein $R_1$ and $R_2$ are individually selected from the group consisting of a substituted or unsubstituted lower alkyl of 1–8 carbon atoms or a substituted or unsubstituted phenyl group. The photochromic compounds are responsive to light in the visible and ultraviolet region of the spectrum.

10 Claims, 2 Drawing Figures

PHOTOCHROMIC COMPOSITION CONTAINING A DIPHENYL DIBENZOCHROM-3-ENE

BACKGROUND OF THE INVENTION

This invention relates to imaging methods using a novel group of photochromic compounds. More particularly, this invention relates to a novel group of photochromic compounds characterized by their ability to change and retain their color upon exposure to visible and ultraviolet light. Still more particularly, this invention relates to various novel compositions of matter comprising various materials having dispersed throughout the body thereof at least one of said photochromic compounds.

Photochromic compounds are well-known in the art, as is the usage thereof for such applications as temporary data storage devices, reflectants for incident high-intensity radiation, optical filters and the like. Generally, the prior art photochromic compounds become colored or change color upon exposure to ultraviolet light and automatically revert to their original color when they are removed from the ultraviolet light or stored in the dark. Various other photochromic compounds, however, change color only when exposed to a high degree of irradiation, such as 10–25 cal/cm²/sec or more, and as such, sunlight (0.2 cal/cm²/sec) will not affect them.

It is usually the reversible nature of the photochromic process which has made it attractive, particularly in the case of memory devices. Ironically, photochromic compounds in spite of many obvious advantages have not found complete acceptance primarily for two reasons, the second of which is surely a consequence of the first such as follows.

a. Activation or coloration of photochromic compounds usually requires the use of light in the ultraviolet region of the electromagnetic spectrum;

b. True reversibility has not been realized with known photochromic compounds. Cyclic fatigue manifests itself as a cessation of photochromic activity after a number of write-erase cycles, short of that required for effective and economical use of these materials.

The first of these problems, that of ultraviolet exposure required for activation, has the obvious technical disadvantage of requiring ultraviolet transmitting components in optical systems used for an imaging process built around photochromics. The cost of such components, were they even available or feasible, would likely more than offset any potential benefit derived from the photochromic material. Thus, the desirability of using photochromic compounds which respond to visible light becomes apparent. Also, the failure of known photochromic compounds to retain their color for more than a few minutes after being subjected to ultraviolet light seriously detracts from their applicability for many commericial and industrial uses. Of prime importance is the need for compounds of this type which can be utilized for permanent or long-term information storage.

SUMMARY OF THE INVENTION

It is, therefore, an object of this invention to provide a novel group of photochromic compounds devoid of the above-noted deficiencies.

It is further an object of the present invention to provide a novel group of photochromic compounds characterized by their ability to change and retain their color in response to ordinary sunlight.

It is a further object of the present invention to provide novel compositions of matter comprising various binder materials having dispersed throughout the body thereof, at least one novel photochromic compound.

It is still further an object of the present invention to provide an imaging member comprising a novel photochromic compound, which is sensitive to both visible and ultraviolet light.

The above objects and others are obtained in general by forming a novel photochromic compound having the formula:

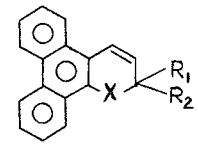

wherein X is oxygen, sulfur or selenium, and $R_1$ and $R_2$ are individually defined as (1) an alkyl group, preferably a lower alkyl of 1–8 carbon atoms exemplified by methyl, propyl or octyl, or the alkyl group may be substituted with radicals such as a nitrate, a sulfate, a sulfonate, a hydroxyl, a carboxyl, a phenyl or a phosphate or (2) phenyl group such as phenyl or substituted phenyl including a lower alkyl phenyl, a halophenyl or a lower alkylene substituted phenyl represented respectively as:

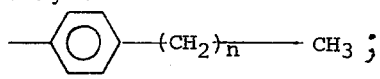

wherein $n$ is 0–3.

Photochromic compounds have been discovered which are responsive to light in the visible region of the spectrum. This invention describes the preparation and characteristics of novel photochromic materials and compositions which are suitable for use in cyclic imaging systems or bioptic memory storage devices in which an unactivated colorless state is activated by actinic radiation to a colored activated state which will persist for a definite period of time. It is a further attribute of these novel photochromic compounds that they may be converted by actinic electromagnetic radiation to more than one colored activated state, where said colored activated states are distinguished by differing degrees of persistence.

Therefore, imaging members using the present compounds or compositions thereof can be used in an imaging process in which light from one region of the spectrum, for example, ultraviolet may be used to record information as either a real colored image or a latent electrostatic image which has a relatively short persistence. On the other hand, use of imaging light in the visible region of the spectrum allows creation of either a real or latent image where the recorded information persists for a relatively long period of time. Such a member may be used in a cyclic imaging process or memory storage devices where portions of the recorded or displayed information are to be frequently updated and other portions must be maintained for long periods of time, or permanently. Stated otherwise, by wavelength selectivity information may be recorded on a single imaging member both permanently and for short periods of time.

More specifically, and by way of example, to illustrate the present invention, 2,2-diphenyl-(5,6), (7,8)-dibenzochrom-3-ene, may be synthesized as follows: 9,10-phenanthrene-quinone is purified by multiple recrystallization, and dried in vacuo. The quinone is reduced with LiAlH$_4$ to give 9,10-dihydroxyphenanthrene which is then dehydrated in refluxing acetic/sulfuric acid to give 9-phenanthrol. The phenanthrol is condensed with ethyl propiolate to obtain [5:6], [7:8]-dibenzocoumarin. The dibenzocoumarin (1 mole) is then reacted with phenylmagnesium bromide (3 moles), which gives the previously unknown 2,2-diphenyl-(5,6), (7,8)-dibenzochrom-3-ene.

A clear film of 2,2-diphenyl-(5,6), (7,8)-dibenzochrom-3-ene is formed on glass slides and then exposed to an image with actinic electromagnetic radiation. This exposure source may constitute a source of visible light, ultraviolet light, X-ray or any other radiation source which is capable of converting the particular photochromic compound from one form to the other. After image-wise conversion of at least a portion of the photochromic layer from one state to the other, the photochromic layer is charged, and because of the marked difference in charge tranporting ability between the two states of the same photochromic compound a latent electrostatic image is formed on the photochromic layer. It should be emphasized here that the exposure must only convert enough photochromic molecules to produce a significant difference between the electrical properties of the exposed and unexposed areas. Because of the relatively small number of molecules which must be converted to fulfill this requirement, with some materials a visible color change need not necessarily be produced in all instances. This latent image on the photochromic layer is then developed by the deposition thereon of finely divided colored electroscopic developing material. Charging and exposure may also be carried out simultaneously. Once the image is developed it may be rendered permanent on the photochromic imaging layer by heat or solvent vapor fusing of the developing particles thereto or the pattern of particles may be transferred to another surface and fixed thereon. Where transfer is employed the layer may be used as an electrostatic printing plate by repeating the charging, developing and transfer steps. Since the exposed areas of the layer remain in the excited photochromic state for a finite period which is fairly long, repeated uniform charging of this layer results in the repeated formation of a charge pattern corresponding to the original exposure. Any time a charge in the pattern is desired the photochromic may be uniformly converted to one form or another and then reimaged as described above. In some cases, the photochromic compound may be imagewise exposed with ultraviolet light while erasure is effected with visible light. As described hereinafter, the photochromic compounds of the instant invention may be imagewise exposed with visible light, and erasure effected with infrared (thermal) illumination.

The photochromic layer may be composed solely of one or more photochromic compounds providing that at least one state of the photochromic compounds has the requisite resistivity to hold the charge pattern long enough for development to take place. For convenience, however, the photochromic material will generally be dispersed or dissolved in solid solution in an insulating resin. This resin may be thought of as a binder or matrix for the photochromic material. Moreover, since photochromic compounds are relatively expensive, the use of the resins also serve to decrease the overall cost of the imaging layer.

BRIEF DESCRIPTION OF THE DRAWING

In order that the invention will be more clearly understood, reference is made to the accompanying drawings in which an embodiment of the invention is illustrated by way of example and in which.

Figure 1:
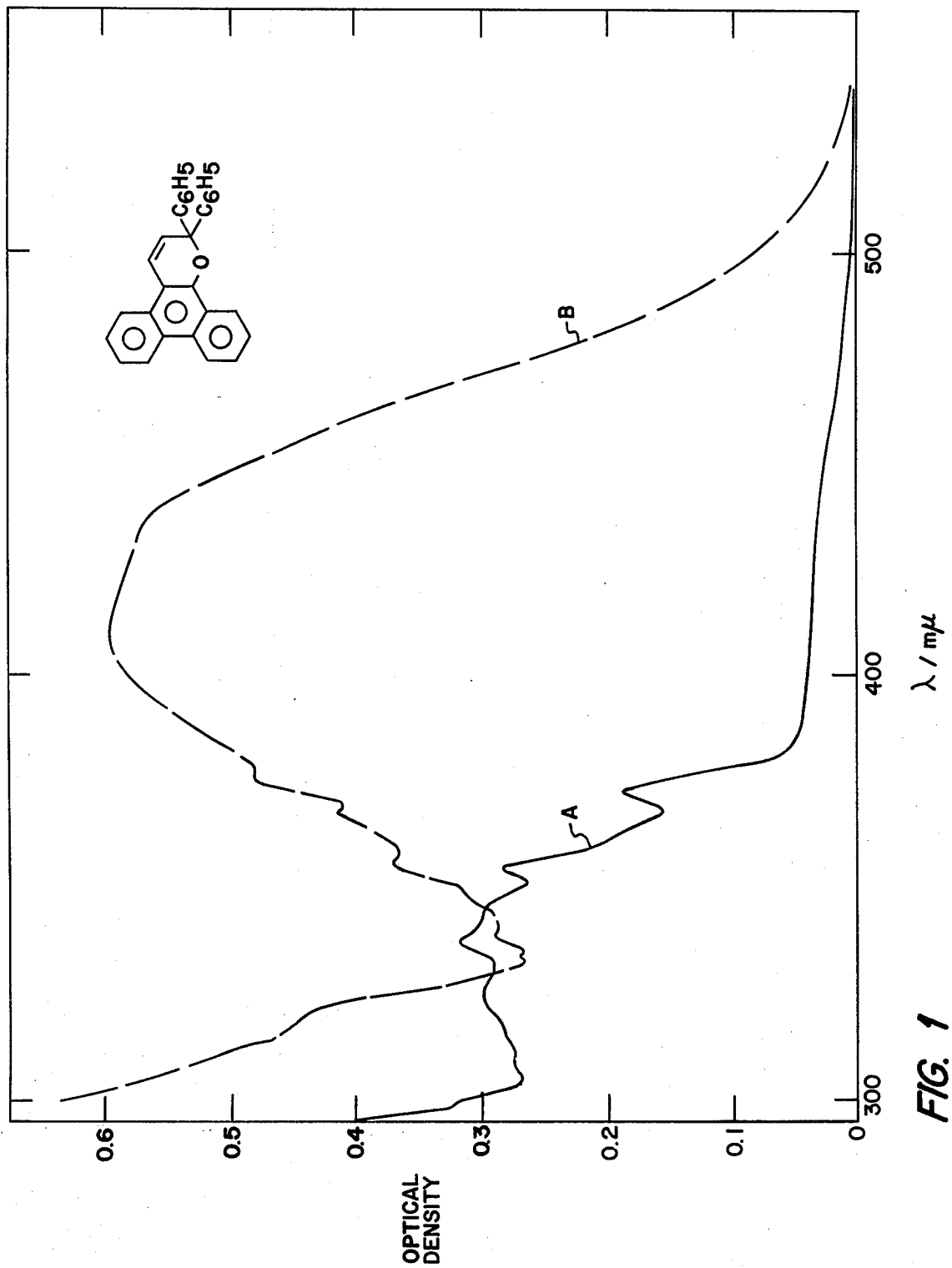
FIG. 1 is the absorption spectra of the activated and unactivated forms of 2,2-diphenyl-(5,6), (7,8)-dibenzochrom-3-ene after exposure to visible or ultraviolet light.

For the purpose of further illustrating the compounds of this invention, the absorption curve of 2,2-diphenyl-(5,6), (7,8)-dibenzochrom-3-ene in the unactivated state is shown in FIG 1, curve A. The absorption spectrum for the compound is highly structured in the region 300–400 m$\mu$ with a coefficient of extinction of $\sim 5 \times 10^3$ 1 mole$^{-1}$cm$^{-1}$. A long weak tail persists into the visible. Below 300 m$\mu$, strong transitions are observed at 250 m$\mu$ with $\epsilon 250 > 6 \times 10^4$ 1 mole$^{-1}$ $^{cm-1}$. At room temperature, these same features are observed in the spectra of the chromene in both alcoholic and hydrocarbon solvents. At higher concentrations, the weak visible absorption in the Figure emerges as a broad transition centered at 430 m$\mu$.

Photolysis of 2,2-diphenyl-5,6), (7,8)-dibenzochrom-3-ene in EPA at 77°K using the total output of a G.E. S-4 Sunlamp produces a deep yellow coloration of the glass. The absorption spectrum of this photocolored solution is shown in FIG. 1, curve B. The dominant feature is a borad structureless band between 350–500 m$\mu$. A maximum in the optical density at 430 m$\mu$ is reached with a 60 minute exposure. This band remains unchanged at 77°K, after the cessation of photolysis. A similar change in visible absorption is observed on photolysis of fluid solutions of the chromene at room temperature. Concommitant with growth of the band at 430 m$\mu$ is a diminution of the intensity of the 250 m$\mu$ transition. On the assumption that the observed photolytic effect corresponds to a one-to-one conversion of a colorless to a colored species, the extinction coefficient of the colored compound can be estimated by measuring simultaneously, the changes in the optical densities at 250 and 430 m$\mu$ for the chromene in 3-methylpentane. It is not possible, however, to determine that the change at 250 m$\mu$ represents only disappearance of the colorless chromene, and not simultaneous enhancement of a weaker transition in the colored moiety. Thus, an upper limit for $\epsilon_{430}$ is calculated to be $6.3 \times 10^4$ 1 mole$^{-1}$cm$^{-1}$.

Disappearance of the photoinduced colored band in the dark is found to occur via a first order kinetic route at 25°C, after removal of the excitation light. In hydrocarbon solvents, the rate constants (half-time) for dacay of the 430 m$\mu$ transition is calculated to be $k_{r_1} = (3.9 \pm 0.5) \times 10^{-3}$ sec$^{-1}$ ($\sim 3$ minutes). Disappearance of this transient absorption, however, does not result in complete bleaching of the yellow coloration. A residual absorption persist in this spectral region for several weeks in the dark.

The most reasonable explanation for the nature of these transient adsorption phenomena involves the photoproduction of the quinone-allide cis (II) and trans (III) isomers:

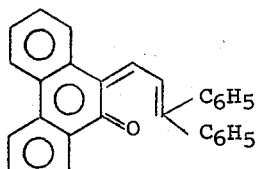

(II)

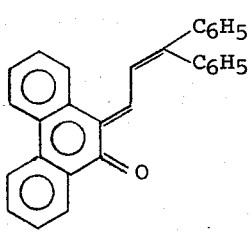

(III)

Reversion of II to I is facile, occuring with a half-time of 3 minutes, while the more extensive isomerization which must precede ring-closure for III is responsible for its much longer half-time, on the order of days.

The small residual absorption in the 430 m$\mu$ region can be observed in all dark equilibrated solutions of I, and is suggestive of a thermally sensitive equilibrium between I and II and/or III. This possibility is confirmed by observing the temperature dependence of the visible absorption of I in both 3-methylpentane and chloroform between 23° and 55°C. Generally an increase in temperature is accompanied by an increase in visible absorption. From the measured absorption at 430 m$\mu$ after dark equilibration (1–2 hours), and the estimated extinction coefficient for the blue absorbing species, equilibrium constants can be calculated at several temperatures. Typical values (25°C) for $K_e$ are $2.3 \times 10^{-3}$ (CHCl$_3$) and $3.6 \times 10^{-3}$ (3-methylpentane). The difference in energy between the colorless and colored species, calculated from the temperature dependence of $K_e$ however, is found to be small: 2.4 kcal mole$^{-1}$ (CHCl$_3$) and 3.6 kcal mole$^{-1}$ (3-methylpentane).

Rapid cooling back to room temperature of a solution which has first been dark equilibrated above ambient temperature, results in almost complete return of the visible absorption to its characteristic room temperature state within several minutes. An added 8–10% absorption change takes place over several days. Thus, the calculated equilibrium parameters refer within approximately 10% to the thermal conversion I ⇌ II. However, it is also clear that the II ⇌ III conversion is thermally accessible at ambient temperatures.

The rate constant $k_{f_1}$ for the process $$I \xrightarrow{k_{f_1}} II$$

can be calculated from $$k_{f_1} = k_{r_1} k_{e_1}$$

and is between $10^{-4}$ to $10^{-5}$ sec$^{-1}$. Thermal formation of III in this system on the time scale of minutes indicates that for $$II \xrightarrow{k_{f_2}} III$$

the rate constant $k_{f_2}$ is only slightly less than $k_{f_1}$, probably of the order of $10^{-5}$ sec$^{-1}$. This, combined with decay constant $k_{r_2}$ of approximately $10^{-5}$ to $10^{-6}$ seconds (based on the lifetime of III after photolysis of I), suggests that the equilibrium $k_{e_2}$ for $$II \underset{\longleftarrow}{\overset{k_{e_2}}{\longrightarrow}} III$$

may be of the order of unity or greater. In other words, a dark equilibrated solution of I contains small amounts of both II and III.

Figure 2:
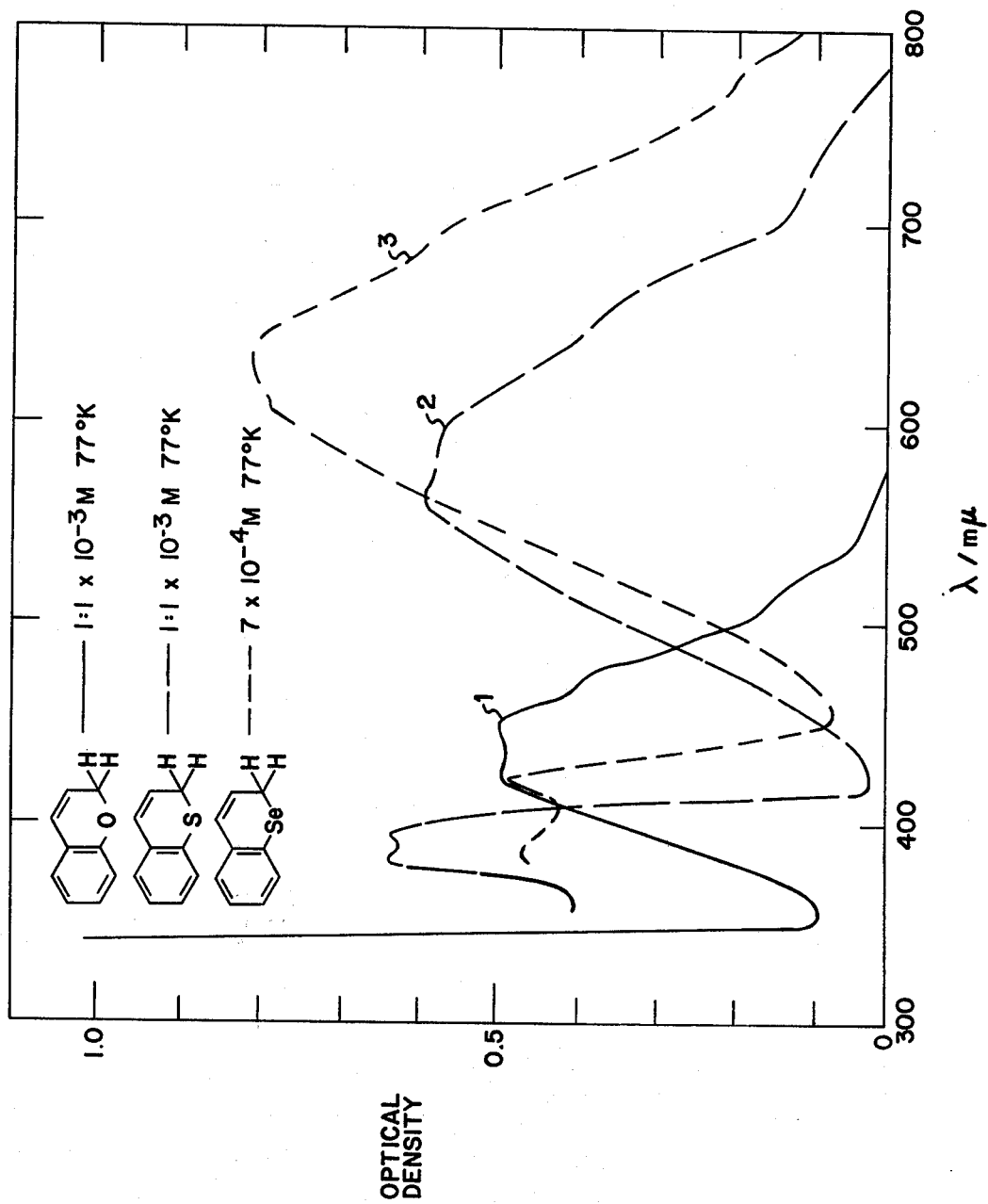
FIG. 2 is the absorption spectra of representative chromene compounds in an EPA (ether:pentane:ethanol; 5:5:2) glass at 77°

The presence of equilibrium amounts of the colored isomers II and III in solutions of I renders these solutions sensitive to visible light. Thus, irradiation of a $3.1 \times 10^{-4}$ M solution of I in 3-methylpentane with visible light at 25°C results in a 21% increase in the optical at 430 m$\mu$. Relaxation of this system to equilibrium in the dark occurs in a half-time of approximately 9 days ($k \sim 10^{-6}$ sec$^{-1}$). It is clear that the effect of visible light is to perturb the equilibrium $$II \rightleftarrows III$$

although it is not unambigous as to the direction of the perturbation. Presumably, both II and III are sensitive to the blue wave-lengths and eventually achievve photostationary concentrations. The possibility of II → I and III → I photo-processes also exists, although these steps would effectively bleach the system if they were important. The observed increase in the 430 m$\mu$ band on visible excitation shows the net formation of a species with a relatively higher visible absorption coefficient. This may be taken as an indication that the process: II $\xrightarrow{h\nu}$ III is dominent. Unfortunately, the observed slow relaxation rate in the dark is also not unequivocal in deciding this question, as the approach to equilibrium in such a system would occur at the same rate from either direction. Although complete spectral analyses for the remaining novel chromene compounds of this invention are not shown, the results are similar to that represented by the data for the 2-H-chromenes in FIG. 2.

Compositions may be formed comprising the novvel photochromic compounds in combination with various film-forming resins and binder materials, the resulting compositions have the photochemical characteristics as described above. These compositions may be applied by coating as a film on a suitable transparent or opaque substrate, or may be self-supporting.

Alternatively, thin films of the photochromic compounds may be formed on suitable substrates by sublimation, such films having the desired properties as stated above.

Any suitable substrate material may be used in accordance with the present invention. Typical non-conductive bases include paper, plastics, polyurethane, polyinychloride, polyethylene, polyethylene terephthalate, among others. Typical conductive bases include NESA glass, aluminized mylar, aluminum, brass, stainless steel, copper, zinc and alloys thereof.

Any suitable film-forming resins may be used to prepare photosensitive compositions with the novel chromenes. Typical examples may include polyesters, polystyrenes, polyhaloethylenes, petroleum hydrocarbons, styrene-acrylonitriles, epoxys, polycarbonates, polysulfones, styrene-butadiene copolymers, phenolics and others such as disclosed in U.S. Pat. Nos. 3,329,502; 3,672,979; and 3,640,710.

As to the binder useable in the present invention, any suitable binder material may be employed. Typical examples include organics such as sucrose and its derivatives, resins and modified resins, etc., non-organic materials such as low melting point insulating glasses including those made from glass forming oxides, sulfides, selenides, borates, phosphates, arsonates, other well known glass formers and mixture thereof. In addition to the above noted materials any other suitable binder may be used if desired. The binder for the present invention should be of such a nature that it will not adversely affect the sensitivity of the photochromic compounds nor will impede the removal or enhancement of color at the time of exposure to an appropriate light source.

While any suitable ratio of the novel photochromic compounds to various film-forming resin and binder materials may be used in the formulation of the present invention, preferred results are obtained when the concentration of the photochromic compound is mixed in amounts ranging from about 1–70 weight percent.

DESCRIPTION OF PREFERRED EMBODIMENTS

EXAMPLE I a. [5:6], [7:8]-dibenzocoumarin is formed as follows: A solution of 3.0 gms 9-phenanthrol, 1.4 gms ethylpropiolate and 4.8 ml concentrated sulfuric acid in 21.5 ml absolute methanol is refluxed for 24 hours. Solution is obtained only when the reaction mixture is warmed to reflux. After refluxing a few minutes, a flocculent precipitate appears, which almost completely redissolves after 30 minutes. At this point, 1.5 ml concentrated sulfuric acid in 8.5 ml absolute ethanol is added and a clear solution is obtained. After 24 hours, a fine precipitate having a pink coloration begins to appear. This solid is collected and recrystallized from an ethanol/acetone mixture, followed by two recrystallizations from benzene. Thin layer chromatography shows one component. 1.8 gms of white crystalline solid (mp 217°–218°C) is recovered. Elemental analysis gives % C=82.76 and % H=3.88. $C_{12}H_{10}O_2$ requires % C = 82.91, and % H = 4.08.

b. 2,2-diphenyl-[5:6], [7:8]-dibenzochrom-3-ene is formed as follows: A Grignard reaction is carried out under a dry nitrogen atmosphere. 0.3 gm of magnesium turnings is suspended in 50 ml of absolute ether, and a small crystal of iodine added. 1.4 ml of bromobenzene is added, the resulting reaction mixture refluxed until solution is completed, and the solution cooled to room temperature. 1.2 gms of [5:6], [7:8]-dibenzocoumarin dissolved in 75 ml dry benzene is added dropwise to the Grignard solution. This reaction mixture is refluxed for 1 hour, cooled with an ice bath and decomposed by the dropwise addition of 50 ml of 22% ammonium chloride. The resulting mixture is steam distilled to remove any biphenyl and other azeotropic by-products. The nonvolatile aqueous portion is cooled to room temperature and an oily brown precipitate is separated by decanting the water. The oily residue is washed twice with ether. The ether isoluble residue is recrystallized twice from glacial acetic acid, and then from acetone, and washed twice with cyclohexane. 0.7 gm of a white crystalline solid, mp 186°–188°C, is recovered. Thin layer chromatography shows one component. Elemental analysis gives: % C = 90.48, % H = 5.51 and % O = 4.22. $C_{29}H_{20}O$ requires % C = 90.59, % H = 5.24 and % O = 4.16. Nuclear magnetic resonance and infrared spectroscopy also confirm the structure.

EXAMPLE II

A toluene solution of the dibenzochrom-3-ene produced according to Example I is mixed with polystyrene such that the weight ratio of chromene to the polymer is 2:1. As amorphous clear film is dip-coated on glass slides from this solution, and the slides are oven dried at 45°C. A film thickness, of 0.5 – 1.0 $\mu$m is measured by interference microscopy. The ultraviolet photosensitivity of the film is confirmed by exposing the clear transparent film to an excitation flash from a Xenon lamp, or a G.E. S-4 sunlamp. In both cases, a deep yellow coloration is produced. The yellow coloration persists for several minutes after cessation of exposure.

EXAMPLE III

A film is prepared as in Example II, but on aluminum rather than glass plates. The film is imagewise exposed to an excitation flash from a Xenon flash tube. A yellow image is seen to form on the film. The film is charged by passing under a three wire corotron held at 8000 volts positive with respect to the aluminum substrate. The film is developed with cascade developer containing electroscopic marking material.

EXAMPLE IV

A solution of the dibenzochrom-3-ene produced according to Example I is prepared in 3-methylpentane such that the concentration of chromene is $3.1 \times 10^{-4}$ M. The optical density of this solution in a 10 cm spectrophotometric cell is 0.85 at 430 m$\mu$. The entire cell is irradiated at 25°C with optically filtered light from a Sylvania Type DWY Tungsten Iodine lamp for 50 minutes. The filters for the irradiation source are Corning 3-71 to prevent exposure with light of $\lambda < 460$ m$\mu$, and a 10 cm water filter to reject infrared wavelengths. The optical density of the solution at 430 m$\mu$ increases to 1.03. The optical density diminishes spontaneously to 0.85 after storage of the solution in the dark for ~ 9 days at 25°C. The time for spontaneous diminution of optical density at 430 m$\mu$ for a similarly irradiated solution is decreased by storage in the dark at temperatures above 25°C.

EXAMPLE V

A clear film is formed according to Example II above except the photosensitivity of the film is confirmed by exposure to visible light, according to the procedure of Example IV.

EXAMPLE VI

A clear compact amorphous film of I is formed on a glass substrate by sublimation of I in vacuo at $10^{-5}$ mm Hg pressure. The photosensitivity of this film to ultraviolet, and to visible light, is confirmed according to the procedures of Examples II and IV.

EXAMPLE VII

A mixture of potassium-9-phenanthrene sulfonate and phosphorous pentachloride is treated with phosphorous oxychloride and heated at 140°C under reflux. The oxychloride is removed by distillation. The semisolid mass is treated with ice-water for an extended period. The solid is collected by filtration and thoroughly washed with water. 9-phenanthrenesulfonyl chloride is mixed with zinc dust and diluted sulfuric acid is added to the mixture. After the initial vigorous reaction, the reaction mixture is heated on a water bath for several hours with stirring. After cooling, the mixture is filtered and the residue extracted with ether. The ethereal extracts are dried over anhydrous magnesium sulfate and the ether removed by evaporation on a rotating evaporator. The 9-phenanthrenethiol is recrystallized from alcohol several times (mp 67°C). 9-phenanthrenethiol is reacted with $\beta,\beta$-diphenylacryloyl-chloride in the presence of magnesium and benzene. This reaction mixture is refluxed for several hours, cooled and filtered. The 9-thiophenanthryl-$\beta,\beta$-diphenylacrylate and aluminum chloride are heated together at 140°–150°C for 2 hours; after acidic decomposition and ether extraction an oily residue is recovered. This residue is refluxed in ethanol and 3% hydrochloric acid for 24 hours. After evaporation of the solvent, the residue is saturated with ammonium sulfate. The product is isolated with ether and is chromatographed on alumina with benzene giving 2,2-diphenyl-[5:6]; [7:8]-dibenzothiochroman-4-one.

2,2-diphenyl-[5:6], [7:8]-dibenzothiochroman-4-one in benzene is added to a suspension of lithium aluminum hydride in ether by dropwise addition and refluxed for 1 hour. The 2,2-diphenyl-[5:6], [7:8]-dibenzothiochroman-4-ol is obtained by the addition of diluted sulfuric acid, extracted with ether and recrystallized from a benzene/petroleum ether mixture.

2,2-diphenyl-[5:6], [7:8]-dibenzothiochroman-4-ol is boiled with acetic acid for 30 minutes. The reaction mixture is poured into water, the product is isolated with ether and recrystallized from a suitable solvent to give pure 2,2-diphenyl-[5:6], [7:8]-diphenyl-[5:6], [7:8]-dibenzothiochrom-3-ene.

EXAMPLE VIII 2,2-diphenyl-[5:6], [7:8]-dibenzoselenochrom-3-ene is formed as follows: 3-bromophenanthrene is reacted with magnesium in ether to give a Grignard reagent which is then reacted with powdered selenium. The reaction mixture is warmed to reflux which is maintained without heating during the addition of the selenium. After the reaction is complete the reaction mixture is poured onto ice, and hydrochloric acid (sp.g. 1.18) is added with stirring. The cold mixture is filtered through glass wool into a separatory funnel and the aqueous phase extracted with ether. The ether extracts are dried over anhydrous magnesium sulfate, where the ether is removed and the 9-selenophenanthrol is isolated.

9-selenophenanthrol is reacted with $\beta,\beta$-diphenylacryl-oxylchloride while refluxing for several hours in the presence of magnesium and benzene, cooled and filtered. The 9-selenophenanthryl-$\beta,\beta$-diphenylacrylate is isolated by crystallization.

9-selenophenanthryl-$\beta,\beta$-diphenylacrylate and aluminum chloride are heated together at 140°–150°C for 2 hours; after acidic decomposition and ether extraction an oily residue is recovered. The residue is refluxed in ethanol and 3% hydrochloric acid for 24 hours. After evaporation of the solvent, the product is isolated with ether and chromatographed on alumina with benzene giving 2,2-diphenyl[5:6], [7:8]-dibenzoselenochroman-4-one.

2,2-diphenyl-[5:6], [7:8]-dibenzoselenochroman-4-one in benzene is reduced with lithium aluminum hydride in ether. The alcohol is isolated by the addition of dilute sulfuric acid, extracted with ether and recrystallized from a suitable solvent to give 2,2-diphenyl-[5:6], [7:8]-dibenzoselenochroman-4-ol.

2,2-diphenyl-[5:6], [7:8]-dibenzoselenochroman-4-ol is refluxed in acetic acid for 30 minutes. The reaction mixture is poured into water, the product is isolated with ether and recrystallized from a suitable solvent to give 2,2-diphenyl-[5:6], [7:8]-dibenzoselenochrom-3-ene.

EXAMPLE IX

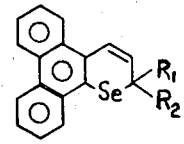

[5:6], [7:8]-dibenzoselenochrom-3-enes are formed as follows: 9-acetyl-phenanthrene is nitrated at 25°C in acetic anhydride with acetyl nitrate, or at 10°C with a solution of fuming nitric acid in acetic anhydride. In either case, after 24 hours the solution is poured into a mixture of crushed ice and dilute sulfuric acid. The organic material is extracted with chloroform and chromatographed with a suitable solvent mixture (e.g., petroleum ether/chloroform) on alumina and the mixed nitroacetylphenanthrenes are separated by collecting chromatographic fractions. This is followed by crystallizations from benzene and from acetic acid.

The pure 9-acetyl-10-nitrophenanthrene is reduced with hydrazine and Raney nickel to give 9-acetyl-10-aminophenanthrene. This is purified by recrystallization from toluene.

A solution of 9-acetyl-10-aminophenanthrene in a mixture of concentrated hydrochloric acid and water (1:1) at 0°C is diazotized with an aqueous solution of sodium nitrite in the usual manner. The strong acid-diamonium salt solution is mixed with anhydrous sodium acetate until Congo red paper no longer turns blue. To this buffered solution, at 0°C, with vigourous stirring, a solution of calcium selenocyanide is added dropwise. During the addition of calcium selenocyanide nitrogen gas is generated, and impure 9-acetyl-10 selenocyanophenathrene separates out simultaneously. After 8 hours, the product is collected by filtration and washed with water. It is then dried on procelain plates and recrystallized from petroleum ether/benzene and charcoaled.

A solution of 9-acetyl-10-selenocyanophenanthrene in chloroform is treated dropwise with a solution of bromine in chloroform. The reaction mixture is stirred gently at room temperature for 24 hours. After evaporating the solvent, the residue is recrystallized from ethanol until pure 9-acetyl-10-bromoselenophenanthrene is obtained.

Zinc dust is added slowly in small portions to a boiling solution of 9-acetyl-10-bromoselenophenanthrene in anhydrous toluene with stirring. The insoluble material is filtered off. Some almost pure 9,9-diacetyldiphenanthrylselenide crystallizes out. The bulk is found in the residue, which is extracted many times with boiling absolute ethanol. The extracts are combined and 9,9-diacetyldiphenanthrylselenide separates out.

While refluxing, zinc dust is added to a suspension of 9-9-diacetyldiphenanthrylselenide in 20% sodium hydroxide over a 2 hour period. 9,9-diacetylphenanthrylselenide is reductively cleaved and dissolves as the sodium salt of 9-acetyl-10-selenophenanthrol. The zinc dust is removed from the suspension by filtration, and after cooling the filtrate, dimethylsulfate is added dropwise. The solution becomes cloudy and with gentle heating a flocculent precipitate separates which is collected by filtration, recrystallized and charcoaled from petroleum ether/benzene to give 9 -acetyl-10-methylselenophenanthrene.

9-acetyl-10-methylselenophenanthrene is dissolved in acetic acid and piperidine with an appropriate aldehyde or ketone and the reaction mixture refluxed for 6 to 8 hours. If possible, excess aldehyde or ketone is removed by steam distillation. Otherwise, the reaction mixture is poured into water and the solids separated by decanting the water. The product is purified by chromatography and recrystallized from ethanol.

By using the following aldehydes or ketones $R_1$ and $R_2$ become:

| Aldehyde or Ketone | | Substituents |
|---|---|---|
| (1) | Benzaldehyde | $R_1 = C_6H_5$ |
| | | $R_2 = H$ |
| (2) | Benzophenone | $R_1, R_2 = C_6H_5$ |
| (3) | Benzylidene acetone | $R_1 = C_6H_5 CH = CH—$ |
| | | $R_2 = CH_3$ |
| (4) | Halosubstituted (x) | $R_1 = C_6H_5$ |
| | Benzophenone | |
| | | $R_2 = C_6H_4x$ |

The above product is cyclized by dissolving in acetic acid and then adding a bromine saturated acetic acid solution. The reaction mixture is refluxed for 1 to 4 hours and after cooling 2,2-disubstituted-[5:6], [7:8]-dibenzoselenochroman-4-one is precipitated with water, collected by filtration and recrystallized from a suitable solvent.

The substituted-[5:6], [7:8]-dibenzoselenochroman-4-one is converted to the alcohol and dehydrated to the chromene as given in the previous examples.

EXAMPLE X

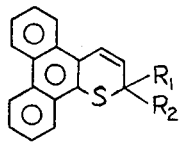

Preparation of [5:6], [7:8]-dibenzothiochrom-3-enes: 9-acetyl-10-aminophenanthrenehydrochloride is diazotized in ice-water with an aqueous solution of sodium nitrate at 0°C. The diazonium salt solution is added dropwise to an aqueous solution of potassium ethyl xanthate with stirring at 40°–45°C and stirring is continued for 30 minutes. The reaction mixture is extracted with ether. The combined extracts are washed with water and 10% sodium hydroxide, and dried over anhydrous magnesium sulfate. The solvent is evaporated, the residue is added to an ethanolic solution of potassium hydroxide. This mixture is refluxed for 10 hours. The solvent is removed under reduced pressure, and water is added to the residue which is then extracted with ether. The aqueous solution is acidified with 30% sulfuric acid in a stream of nitrogen gas and the 9-acetyl-10-thiophenanthrol separates out. This is extracted with ether; the combined ether extracts are washed with water and dried over anhydrous magnesium sulfate. After evaporation of the solvent, the 9-acetyl-10-thiophenanthrol is purified by recrystallization and stored under nitrogen to prevent oxidation to the disulfide.

The 9-acetyl-10-thiophenanthrol and the appropriate aldehyde or ketone according to Example IX are dissolved in benzene. This misture is added to a well stirred benzene solution of sodium t-butoxide at a rate of 1 drop per second. The resulting mixture is refluxed with stirring for 20 hours, then poured into a mixture of hydrobromic acid (3 parts) and acetic acid (2parts). The benzene layer is steam distilled to remove any residual azeotropic starting materials and solvent. The gummy residue is refluxed in a hydrogen chloride saturated methanol solution for 0.5 to 1 hour to drive the cyclization to completion. After removing the solvent, the product 2,2-diphenyl-[5:6], [7:8]-dibenzothiochroman-4-one is purified by chromatography and recrystallization from ethanol and water.

The above chromanone is reduced to 2,2 diphenyl-[5:6], [7:8]-dibenzothiochroman-4-ol by addition to a methanolic solution of sodium borohydride. Decomposition of the reaction mixture with water yields a gummy solid which is purified by recrystallization. The chromanol is converted to the chromene derivative by fusion with finely powdered freshly fused potassium hydrogen sulfate at 220°C. The product is purified by chromatography and recrystallization from a benzene-petroleum ether solvent system.

EXAMPLE XI

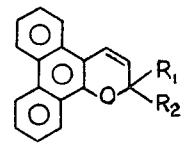

Oxygen derivatives analogous to those of Examples IX and X may be prepared as follows: 9-acetyl-10-hydroxyphenanthrene and the appropriate aldehyde or ketone according to Example IX in benzene are added to a solution of sodium t-butoxide in benzene and the resulting mixture refluxed for 20 hours with stirring. The reaction mixture is poured into a stirred solution of hydrobromic acid (3 parts) and acetic acid (2 parts). The benzene layer is steam distilled and the residue boiled with methanol saturated with dry hydrogen chloride 0.5–1 hour to drive the cyclization to completion. After the solvent has been removed, the chroman-4-one is isolated by chromatography and crystallization from petroleum ether solvent.

The chromanone is reduced to the chroman-4-ol by the action of sodium borohydride in methanol. Decomposition of the reaction mixture by water gives a gummy solid which is purified by recrystallization. The purified chromanol is heated at 220°C with finely powdered freshly fused potassium hydrogen sulfate. The residue is chromatographed and the recovered chromene purified by recrystallization from acetone.

Although specific compounds have been stated in the above description of preferred embodiments, other derivatives of the same compounds may be used with similar results. In addition other materials may be added to the mixture to synergize, enhance, or otherwise modify its properties. For example, dye sensitizers may be added to the photochromic compositions or photochromic compounds to broaden the spectral response of the materials. Other modifications and ramifications of the present invention will occur to those skilled in the art upon a reading of the disclosure. These are intended to be included within the scope of this invention.

What is claimed is

1. A photochromic composition comprising a compound having the formula:

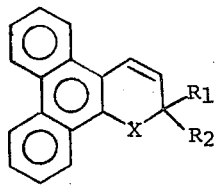

wherein X is selected from the group consisting of oxygen, sulfur and selenium; and wherein $R_1$ and $R_2$ are individually selected from the group consisting of a substituted or unsubstituted lower alkyl of 1–8 carbon atoms a phenyl group or a substituted phenyl group and a film forming resin.

2. An imaging member comprising a transparent film substrate having superimposed thereon a homogeneous thin film of a compound having the formula:

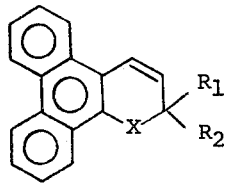

wherein X is selected from the group consisting of oxygen, sulfur and selenium; and wherein $R_1$ and $R_2$ are individually selected from the group consisting of a substituted or unsubstituted lower alkyl of 1–8 carbon atoms, a phenyl group or a substituted phenyl group.

3. An imaging member according to claim 2 wherein the photochromic compound is admixed with a film forming resin.

4. A photochromic composition comprising a compound according to the formula:

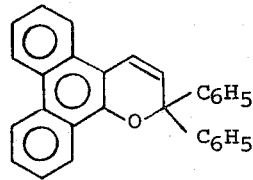

and polystyrene.

5. A photochromic composition comprising a compound according to the forumla:

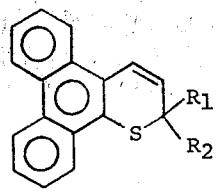

wherein $R_1$ and $R_2$ are individually selected from the group consisting of lower alkyl of 1–8 carbon atoms, phenyl, substituted phenyl and a film forming resin.

6. A photochromic composition comprising a compound according to the formula:

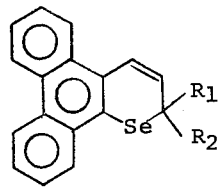

wherein $R_1$ and $R_2$ are individually selected from the group consisting of lower alkyl of 1–8 carbon atoms, phenyl, substituted phenyl and a film forming resin.

7. An imaging member comprising a supporting substrate having superimposed thereon a homogeneous thin film of a photochromic compound having the formula:

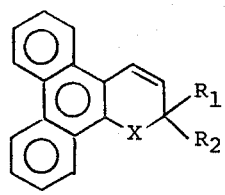

wherein X is selected from the group consisting of oxygen, sulfur and selenium; and wherein $R_1$ and $R_2$ are individually selected from the group consisting of a substituted or unsubstituted lower alkyl of 1–8 carbon atoms, a phenyl group or a substituted phenyl group.

8. An imaging process for forming a plurality of images comprising the steps of:
a. providing an imaging member comprising a support substrate having superimposed thereon a homogeneous thin film of a selectively activated photochromic compound which is capable of at least two activated states wherein each state is distinguishable by different degrees of persistence having the formula:

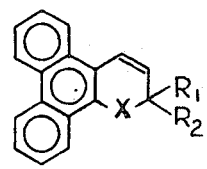

wherein $x$ is selected from the group consisting of oxygen, sulfur and selenium; and wherein $R_1$ and $R_2$ are individually selected from the group consisting of a substituted or unsubstituted lower alkyl of 1–8 carbon atoms, phenyl, substituted phenyl and, b. imagewise exposing said imaging member to electromagnetic radiation suitable for transforming the member to an activated state to form an image.

9. An imaging process according to claim 8, wherein a latent image is formed.

10. An imaging process according to claim 8, wherein a visible colored image is formed.

* * * * *

UNITED STATES PATENT AND TRADEMARK OFFICE
CERTIFICATE OF CORRECTION

PATENT NO. : 3,973,966
DATED : August 10, 1976
INVENTOR(S) : John B. Flannery and Anita C. Van Laeken It is certified that error appears in the above-identified patent and that said Letters Patent are hereby corrected as shown below:

In the Abstract, line 1, delete "novel imaging imaging comprising" and insert --novel imaging compositions comprising--.

Column 3, line 53, "charge" should be corrected to read --change--.

Column 4, line 19, insert a --K.-- after "77°" to cause it to read --77°K.--.

Column 4, line 34, "2,2-diphenyl-5,6)," should be corrected to read --2,2-diphenyl-(5,6),--.

Column 4, line 39, "borad" should be corrected to read --broad--.

Column 4, line 63, "dacay" should be corrected to read --decay--.

Column 4, line 67, "persist" should be corrected to read --persists--.

Column 5, before formulae (II) and (III) insert formula (I) as follows:

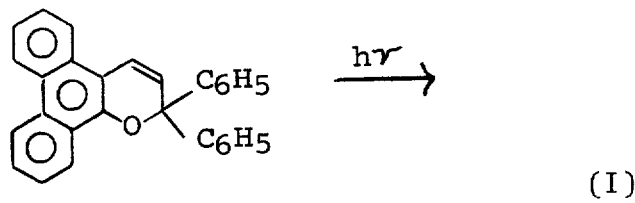

(I)

UNITED STATES PATENT AND TRADEMARK OFFICE
CERTIFICATE OF CORRECTION

PATENT NO. : 3,973,966
DATED : August 10, 1976
INVENTOR(S) : John B. Flannery and Anita C. Van Laeken Page 2 of 2

It is certified that error appears in the above-identified patent and that said Letters Patent are hereby corrected as shown below:

Column 5, line 16, after formula (II) and before formula (III) insert a --+--.

Column 5, line 47, "$K_e$ " should be corrected to read --Kel--.

Column 5, line 51, "$K_e$ " should be corrected to read --$K_{e_1}$--.

Column 6, line 34, "achievve" should be corrected to read --achieve--.

Column 6, line 42, "dominent" should be corrected to read --dominant--.

Column 6, line 51, "novvel" should be corrected to read --novel--.

Column 6, line 65, "polyinychloride" should be corrected to read --polyvinylchloride--.

Column 10, line 49, "diamonium" should be corrected to read --diazonium--.

Column 10, line 51, "vigourous" should be corrected to read --vigorous--.

Column 10, line 57, "procelain" should be corrected to read --porcelain--.

Signed and Sealed this

Second Day of November 1976

[SEAL]

Attest:

RUTH C. MASON
Attesting Officer

C. MARSHALL DANN
Commissioner of Patents and Trademarks